United States Patent [19]

Nudelman et al.

[11] 4,244,885
[45] Jan. 13, 1981

[54] α-SUBSTITUTED-3-(HALOMETHYL)-4-HYDROXYBENZENEACETIC ACIDS

[75] Inventors: Abraham Nudelman, Rehovot; Abraham Patchornik, Ness-Ziyona, both of Israel

[73] Assignee: Yeda Research and Development Co. Ltd., Rehovot, Israel

[21] Appl. No.: 858,724

[22] Filed: Dec. 8, 1977

[51] Int. Cl.³ .................... C07C 59/54; C07C 101/72
[52] U.S. Cl. ................... 260/507 R; 562/442; 562/439; 562/470; 562/478; 544/16; 544/26; 260/239.1
[58] Field of Search ............... 260/519, 507 R; 562/444, 445, 470, 478, 430, 448, 439; 544/16

[56] References Cited

U.S. PATENT DOCUMENTS

| | | | |
|---|---|---|---|
| 2,816,915 | 12/1957 | Gregory | 260/519 |
| 2,824,128 | 2/1958 | Dexter | 260/519 |
| 4,012,380 | 3/1977 | Spry | 544/16 |
| 4,013,651 | 3/1977 | Spitzer | 544/16 |

OTHER PUBLICATIONS

McDonald et al., Chem. Abst., vol. 77, p. 487, #34153g (1972).
Baker et al., Chem. Abst., vol. 83, p. 510, #58856p (1975).
Crast et al., Chem. Abst., vol. 84, p. 473, #164809p (1978).

*Primary Examiner*—Natalie Trousof
*Assistant Examiner*—James H. Reamer
*Attorney, Agent, or Firm*—William J. Stein; George Rauchfuss, Jr.

[57] ABSTRACT

α-Substituted-3-(halomethyl)-4-hydroxybenzeneacetic acids, prepared by the halomethylation of α-substituted-4-hydroxybenzeneacetic acids are new and useful as starting materials for the preparation of cephalosporin and penicillin derivatives.

12 Claims, No Drawings

α-SUBSTITUTED-3-(HALOMETHYL)-4-HYDROXYBENZENEACETIC ACIDS

FIELD OF INVENTION

This invention relates to novel acetic acid derivatives useful as intermediates in the synthesis of penicillins and cephalosporins, and processes for their preparation.

SUMMARY OF INVENTION

Compounds of Formula I are useful as intermediates in the synthesis of penicillins and cephalosporins

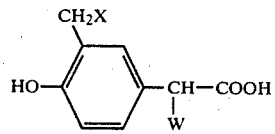

Formula I wherein X is a halogen atom such as chlorine or bromine; W is selected from hydrogen, amino, hydroxy, —SO$_3$H, —COOH or —NHCONHR$_1$ wherein R$_1$ is H, a lower alkyl group of from 1 to 4 carbon atoms and a phenyl group; and acceptable salts thereof.

Within the scope of this invention are included the (—)-isomer, the (+)-isomer or mixtures thereof of compounds of Formula I wherein W is other than hydrogen or —COOH.

DETAILED DESCRIPTION OF INVENTION

Illustrative examples of lower alkyl groups of from 1 to 4 carbon atoms which R$_1$ may represent in Formula I are methyl, ethyl, propyl, isopropyl, n-butyl, sec-butyl, iso-butyl and tert-butyl.

The compounds of Formula I are prepared by halomethylation of a compound of Formula II as described schematically in Reaction I

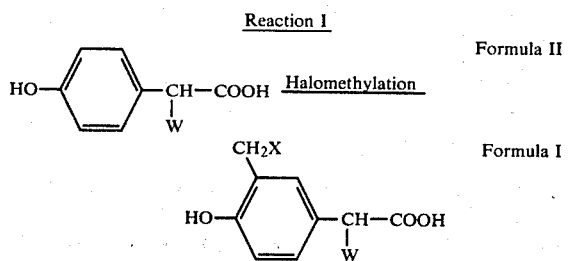

wherein X and W are as defined in Formula I.

The starting materials used in this invention, compounds of Formula II, are either commercially available or are prepared by methods known in the art. Esters of compounds of Formula II, for example, methyl, ethyl, isopropyl or butyl may be prepared by methods well known in the art may be used in the halomethylation reaction.

The halomethylation reaction of compounds of Formula II may be carried out by several methods. For example, compounds of Formula I are formed when an equimolar mixture of a compound of Formula II is reacted with formaldehyde derived from a formalin solution, paraformaldehyde, trioxane, Cl—CH$_2$—OCH$_3$ or dichloromethyl ether, optionally in the presence of a Lewis acid such as ZnCl$_2$, AlCl$_3$, SnCl$_4$, TiCl$_4$ or ClSO$_3$H in a solvent such as water, petroleum ether, a chlorinated hydrocarbon such as methylene chloride, chloroform or ethylene dichloride, an aromatic hydrocarbon such as benzene, toluene or xylene at a temperature ranging from —10° C. to 100° C. for from 0.5 to 10 hours and to which an excess of hydrogen chloride gas or hydrogen bromide gas is added.

Illustratively, the reaction of equimolar amounts of an acid of Formula II and 34–38% formalin in concentrated hydrochloric acid or hydrobromic acid at temperatures ranging from —10° to 100° C. during which time an excess of hydrogen chloride gas or hydrogen bromide gas is added to the reaction mixture for a period of from 0.5–10 hours also yields compounds of Formula I.

Illustratively, upon reaction of equimolar amounts of an acid of Formula II and trioxane in acetic or phosphoric acids at temperatures of from —10° to 100° C. for a period of time of from 0.5 to 10 hours during which an excess of hydrogen chloride gas or hydrogen bromide gas is added to the reaction mixture, compounds of Formula I are obtained.

Illustratively, the reaction of equimolar amounts of an acid of Formula II in the presence of a catalytic amount of Lewis acids, such as those described hereinabove, with chloromethyl methyl ether or dichloromethyl ether at temperatures from —10° to 100° C., for a period of from 0.5 to 10 hours, in acetic or sulfuric acid to which hydrogen chloride gas or hydrogen bromide gas is added, will give compounds of Formula I.

The preferred conditions of the reaction are those where an equimolar amount of 34–38% formalin is added to a compound of Formula II dissolved in a minimum amount of concentrated hydrochloric or hydrobromic acid at a temperature of from —10° to 45° C., and to the solution thus obtained hydrogen chloride gas or hydrogen bromide gas is added for a period of 0.5 to 10 hours, to give the compound of Formula I.

When the reaction conditions hereinbove described are used high yields of products of Formula I are obtained. These products are devoid of impurities such as those stemming from the following:

(a) Polynuclear halomethylation,
(b) Halomethylation of 4-hydroxybenzeneacetic acid derivative in other than the 3-position,
(c) Esterification of the —COOH group,
(d) Formylation of the hydroxy group,
(e) Condensation of formaldehyde or derivatives thereof with the amino group of such compounds of Formula I wherein W is amino,
(f) Condensation of the halomethyl group with the —COOH group to give polyesters, or
(g) Condensation of the halomethyl group with an amino group to give a polyamide.

When the starting material is an optically active isomer of a compound of Formula II wherein W is other than hydrogen or —COOH, the compound thus obtained in the halomethylation reaction is optically active.

The preferred compounds of this invention are compounds represented by Formula I wherein X is chlorine or bromine, W is amino, hydrogen, hydroxyl, carboxyl, sulfo and NHCONHR$_1$ wherein R$_1$ is hydrogen, a lower alkyl group of from 1 to 4 carbon atoms or a phenyl group and R is hydrogen. The more preferred compounds are those compounds represented by Formula I wherein X is chlorine or bromine, W is amino.

Acceptable acid addition salts may be prepared by reacting compounds of Formula I where W is amino with either an inorganic or an organic acid. For example, the inorganic acid may be hydrochloric, hydrobromic, hydriodic, sulfuric, phosphoric or sulfamic acid. Organic acids which may be used to form acid addition salts include maleic, acetic, citric, oxalic, succinic, benzoic, tartaric, fumaric, malic, mandelic, ascorbic and trifluoroacetic.

Likewise, acceptable salts may be prepared by reacting the compounds of Formula I with a base. The base may be an alkali metal or an alkaline earth metal compound such as a hydroxide, an oxide, a bicarbonate or a carbonate. The cations may be sodium, potassium, magnesium, calcium or ammonium. In addition, amines such as primary, secondary or tertiary may be used to form salts with the acids as represented by compounds of Formula I. Amines such as ethylamine, dibutylamine, trioctylamine and pyridine may be used.

The α-substituted-3-(halomethyl)-4-hydroxybenzeneacetic acid compounds, prepared by the halomethylation reaction described, may be coupled with 7-aminocephalosporin or 6-aminopenicillin derivatives. For example, an acid compound of the formula

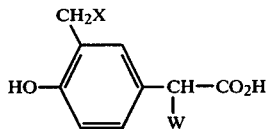

or a functional equivalent thereof where X and W are as described for Formula I may be coupled with a compound of the formula

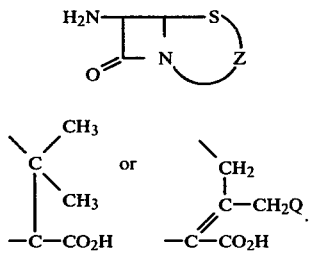

where Z is and Q is, for example, hydrogen, acetyloxy or a heterocyclic thio group such as tetrazol-5-ylthio, 1,3,4-thiadiazol-2-ylthio, or 1,2,3-triazol-5-ylthio in a suitable solvent such as tetrahydrofuran, acetone, water, a chlorinated aliphatic hydrocarbon such as methylene chloride, chloroform or carbon tetrachloride at a temperature of from about −10° C. to about 30° C. for from 15 minutes to 3 hours.

The functional equivalents of the acid compound include the acid halide, for example, the acid chloride, acid anhydrides, including mixed anhydrides with, for example, alkylphosphoric acid, lower aliphatic monoesters of carbonic acid or aryl sulfonic acids.

The cephalosporin and penicillin derivatives thus prepared are useful as antibacterial agents.

EXAMPLE 1

(−)-α-Amino-3-(chloromethyl)-4-hydroxybenzeneacetic acid hydrochloride

To a solution of (−)-α-amino-4-hydroxybenzeneacetic acid (100 g, 0.6 mole) in a minimum amount of concentrated hydrochloric acid at 35°–40° C. is added 50 ml of aqueous formaldehyde (35–37%) (0.6 mole) and the addition of hydrogen chloride gas is begun. After 5–10 minutes, a solid begins to precipitate. Stirring is continued for 30 minutes and the solid is then collected. The crude product is washed with ether and with acetone. A second crop is obtained from the filtrate after standing at room temperature overnight. Collected 102 g (67%) mp>300° C., $[\alpha]_D^{18} = -134°$ (c 4.75, $CH_3OH$) NMR (DMSO-$D_6$) ppm (δ) 4.68 (s,2), 4.9 (broad s,1), 6.9–7.6 (superimposed q and s,3).

Anal. calcd for $C_9H_{10}ClNO_3$ HCl: Cl 28.13; Found 26.44.

In like manner and using equivalent amounts of (−)-α-amino-4-hydroxybenzeneacetic acid, ethyl ester, hydrochloride in place of (−)-α-amino-4-hydroxybenzeneacetic acid gives (+)-α-amino-3-(chloromethyl)-4-hydroxybenzeneacetic acid ethyl ester hydrochloride.

EXAMPLE 2

(−)-α-Amino-3-(bromomethyl)-4-hydroxybenzeneacetic acid hydrobromide

To a solution of (−)-α-amino-4-hydroxybenzeneacetic acid (0.6 mole) in a minimum amount of concentrated hydrobromic acid at 35°–40° C. is added 50 ml of aqueous formaldehyde (35–37%) (0.6 mole). Addition of hydrogen bromide gas is begun. After 5–10 minutes, a solid begins to precipitate. Stirring is continued for 30 minutes. The title compound is collected and washed with ether and acetone.

EXAMPLE 3

3-Chloromethyl-4-hydroxybenzeneacetic acid

4-Hydroxybenzeneacetic acid, 0.5 mole, is added to concentrated hydrochloric acid, 50 ml, then 0.5 mole of formaldehyde in the form of a 34–38% solution of formalin is added. Hydrogen chloride is bubbled through the reaction mixture for 60 minutes while maintaining the temperature of the reaction mixture at 35° to 45° C. The reaction mixture is poured into water and the title compound is extracted from the aqueous solution with ethyl acetate. The ethyl acetate is dried over magnesium sulfate, filtered and removed to give the title compound.

EXAMPLE 4

α-Hydroxy-3-(bromomethyl)-4-hydroxybenzeneacetic acid

About 0.3 mole of α-hydroxy(4-hydroxybenzene)acetic acid is added to about 50 ml of concentrated hydrobromic acid containing about 0.1 mole trioxane. The temperature is maintained between about 35° to about 45° C. while passing hydrogen bromide gas through the reaction mixture. After about 90 minutes, the reaction mixture is poured into cold water and the title compound is extracted with ethyl acetate. After drying the organic extract over magnesium sulfate and filtering to remove the magnesium sulfate, removal of the ethyl acetate gives the title compound.

EXAMPLE 5

α-Carboxy-3-(bromomethyl)-4-hydroxybenzeneacetic acid

About 0.5 mole of 4-hydroxybenzeneacetic acid is dissolved in about 50 ml of anhydrous tetrahydrofuran at −40° C. To this solution is added 3 equivalents of lithium diisopropylamide. The temperature is maintained at about −40° C. for about 15 minutes. Then 1 equivalent of ethyl chloroformate is added and the temperature is raised from about −40° C. to about 20° C. and the reaction mixture stirred for about 60 minutes. The reaction mixture is poured into water and the monoester of α-carboxy-4-hydroxybenzeneacetic acid is recovered from the aqueous solution. Hydrolysis of the half-ester with sodium hydroxide followed by acidification with hydrochloric acid gives α-carboxy-4-hydroxybenzeneacetic acid.

α-Carboxy-4-hydroxybenzeneacetic acid, 0.3 mole, is added to aqueous acetic acid (50%) which contains 0.5 mole of chloromethyl methyl ether and a catalytic amount of zinc chloride. The temperature is maintained between about 35° to 45° C. for about 2 hours while hydrogen chloride gas is bubbled through the solution. The reaction mixture is then added to water and the reaction product is recovered by extraction with methylene chloride. After drying the methylene chloride over magnesium sulfate, the magnesium sulfate is removed by filtration. Removal of the methylene chloride gives the title compound.

EXAMPLE 6

α-Sulfo-3-(chloromethyl)-4-hydroxybenzeneacetic acid

Approximately 0.6 mole of 4-hydroxybenzeneacetic acid is added to about 0.9 mole of dioxane-$SO_3$ complex in ethylene chloride maintained at room temperature. This mixture is then stirred at room temperature for 16 hours. The reaction mixture is poured into water and the α-sulfo-4-hydroxybenzeneacetic acid is recovered from the aqueous solution by evaporation of the dioxane and ethylene chloride.

α-Sulfo-4-hydroxybenzeneacetic acid, 0.3 mole, is dissolved in aqueous sulfuric acid (50%). One equivalent of dichloromethyl ether is added to the solution maintained at between 35° to 45° C. Hydrogen chloride is then bubbled through this reaction mixture for 3 hours. The desired compound is recovered by pouring the reaction mixture into water and extracting the title compound with ethyl acetate. The ethyl acetate is dried over magnesium sulfate. The magnesium sulfate is removed by filtration and evaporation of the ethyl acetate gives the title compound.

EXAMPLE 7

α-(Aminocarbonyl)amino-3-(chloromethyl)-4-hydroxybenzeneacetic acid

To about 0.15 mole of α-amino-4-hydroxybenzeneacetic acid dissolved in 700 ml of water and 0.2 mole of glacial acetic acid is added about 0.2 mole of potassium cyanate. The resulting mixture is stirred at room temperature for about 30 minutes. The reaction mixture is saturated with sodium chloride and then extracted with ethyl acetate. The ethyl acetate is washed with water, dried over magnesium sulfate, filtered and evaporated to give α-(aminocarbonyl)amino-4-hydroxybenzeneacetic acid.

Equivalent amounts (0.1 mole) of α-(aminocarbonyl)amino-4-hydroxybenzeneacetic acid and formaldehyde as a 34–38% formalin solution are added to 250 ml of concentrated hydrochloric acid. The temperature is maintained between 20° to 40° C. and gaseous hydrogen chloride is added over a period of 2 hours. The solution thus obtained is concentrated under vacuum and the residue is extracted with ethyl acetate. The ethyl acetate extract is washed with water, dried over magnesium sulfate and evaporated to give the title compound.

EXAMPLE 8

α-(Methylaminocarbonyl)amino-4-hydroxybenzeneacetic acid

To 0.1 mole of α-amino-4-hydroxybenzeneacetic acid dissolved in 500 ml of water containing 0.05 mole of acetic acid is added 0.11 mole of methyl isocyanate. This mixture is stirred for 30 minutes at room temperature. The reaction mixture is saturated with sodium chloride and then extracted with ethyl acetate. The ethyl acetate is washed with water, dried over magnesium sulfate, filtered and evaporated to give the title compound.

In like manner and using equivalent amounts of reactants, substitution of phenyl isocyanate for methyl isocyanate gives α-(phenylaminocarbonyl)amino-4-hydroxybenzeneacetic acid.

EXAMPLE 9

6-[[Amino[3-(chloromethyl)-4-hydroxybenzene]acetyl]amino]-3,3-dimethyl-7-oxo-4-thia-1-azabicyclo[3.2.0]heptane-2-carboxylic acid (−)-α-Amino-3-(chloromethyl)-4-hydroxybenzeneacetic acid, 0.3 mole, is dissolved in methylene chloride and the hydrochloride salt is formed by passing hydrogen chloride gas into the solution for 20 minutes. Then about 1.5 equivalents of phosphorus pentachloride is added and the mixture is stirred at 0° to 10° C. for about 2 hours. At the end of this time the acid chloride is collected by filtration. (−)-α-Amino-3-(chloromethyl)-4-hydroxybenzeneacetyl chloride hydrochloride (0.1 mole) is added to a solution of 1 equivalent of 6-amino-3,3-dimethyl-7-oxo-4-thia-1-azabicyclo[3.2.0]heptane-2-carboxylic acid in water-tetrahydrofuran containing about 2 equivalents of N,N-dimethylaniline. The mixture is stirred at room temperature for about 3 hours. The tetrahydrofuran is removed under vacuum and the pH of the aqueous phase is adjusted to about 4–5. Upon cooling and diluting with acetonitrile the title compound precipitates.

EXAMPLE 10

7-[[[(3-Chloromethyl)-4-hydroxyphenyl]acetyl]amino]-3-methyl-8-oxo-5-thia-1-azabicyclo[4.2.0]oct-2-ene-2-carboxylic acid 3-(Chloromethyl)-4-hydroxybenzeneacetic acid (1 equivalent) is added to tetrahydrofuran. The reaction mixture is then cooled to −10° C. and 1 equivalent of isobutylchloroformate is added. After 30 minutes at −10° C., 1 equivalent of 7-amino-3-methyl-8-oxo-5-thia-1-azabicyclo[4.2.0]oct-2-ene-2-carboxylic acid in water-tetrahydrofuran containing 1 equivalent of triethylamine is added. After the addition, the reaction temperature is allowed to rise from −10° C. to about 20° C. and maintained at 20° C. for about 60 minutes. Sodium bicarbonate solution is added until the pH is about 4.5 to 5.5. This aqueous solution is then extracted with ethyl acetate. The organic phase is dried over magnesium sulfate and then filtered to remove the magnesium sulfate. Removal of the solvent gives the title compound.

We claim:
1. A compound of the formula

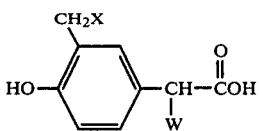

wherein X is chlorine or bromine, W is hydrogen, hydroxy, —SO$_3$H, —CO$_2$H or —NHCONHR$_1$ wherein R$_1$ is H, a lower alkyl group of from 1 to 4 carbon atoms, or a phenyl group; and acceptable salts thereof.

2. A compound of claim 1 which is the (+)-isomer or the (—)-isomer with the proviso that W is other than hydrogen or —COOH.

3. A compound of claim 1 wherein W is hydrogen.
4. A compound of claim 2 wherein W is hydroxy.
5. A compound of claim 2 wherein W is —SO$_3$H.
6. A compound of claim 1 wherein W is —COOH.
7. A compound of claim 2 wherein W is NH—CONHR$_1$ wherein R$_1$ is hydrogen, a lower alkyl group of from 1 to 4 carbon atoms or a phenyl group.
8. A compound of claim 1 which is 3-(chloromethyl)-4-hydroxybenzeneacetic acid or an acceptable salt thereof.
9. A compound of claim 1 which is α-carboxy-3-(chloromethyl)-4-hydroxybenzeneacetic acid or an acceptable salt thereof.
10. A compound of claim 1 which is α-hydroxy-3-(chloromethyl)-4-hydroxybenzeneacetic acid or an acceptable salt thereof.
11. A compound of claim 1 which is α-sulfo-3-(chloromethyl)-4-hydroxybenzeneacetic acid or an acceptable salt thereof.
12. A compound of claim 1 which is α-(aminocarbonyl)-amino-3-(chloromethyl)-4-hydroxybenzeneacetic acid or an acceptable salt thereof.

* * * * *